United States Patent [19]

Au-Young et al.

[11] Patent Number: 5,776,732
[45] Date of Patent: Jul. 7, 1998

[54] HUMAN INDUCED TUMOR PROTEIN

[75] Inventors: Janice Au-Young, Berkeley; Phillip R. Hawkins, Mountain View, both of Calif.

[73] Assignee: Incyte Pharmaceuticals, Inc., Palo Alto, Calif.

[21] Appl. No.: 689,974

[22] Filed: Aug. 16, 1996

[51] Int. Cl.⁶ ................................................ C12P 21/00
[52] U.S. Cl. ............... 435/69.1; 435/252.3; 435/254.11; 435/254.2; 536/23.1; 536/23.5
[58] Field of Search .................. 536/23.1, 23.5; 435/320.1, 240.2, 252.3, 254.11, 240.4, 254.2, 69.1

[56] References Cited

PUBLICATIONS

Accession No. N31858, Hillier et al. (1996) yx71c01.r1 Homo Sapiens cDNA clone 267168 5'.EST Database.
Accession No. Z44998, Auffray et al. (1994) H. Sapiens partial cDNA sequence; clone c-2ed08. EST Database.
Accession No. R12298, Hillier et al. (1995) yf48f11.r1 Homo sapiens cDNA clone 25383 5'. EST Database.
Lebel, M., et al., "Sequence analysis of a novel cDNA which is overexpressed in testicular tumors from polyomavirus large T-antigen transgenic mice" *DNA Seq.*, 5:31–39 (1994).
Vielkind, U., "Genetic Control of Cell Differentiation in Platyfish–Swordtail Melanomas" *J. Exp. Zool.*, 196:197–204 (1974).
Raza, A., et al., "Clinical and Prognostic Significance of In Vivo Differentiation in Acute Myeloid Leukemia" *Amer. J. Hematology*, 42:147–157 (1993).
Dakuor, J. et al., (GI 1293563), GenBank Sequence Database (Accession U49188), National Center for Biotechnology Information, National Library of Medicine, Bethesda, Maryland 20894, 07 Mar. 1996.
Pfeiffer, S.S.E., (GI 310100), GenBank Sequence Database (Accession L20319), National Center for Biotechnology Information, National Library of Medicine, Bethesda, Maryland 20894, 30 Jun. 1993.

*Primary Examiner*—Robert A. Wax
*Assistant Examiner*—Enrique D. Longton
*Attorney, Agent, or Firm*—Lucy J. Billings

[57] ABSTRACT

The present invention provides a polynucleotide which identifies and encodes a novel human induced tumor protein (HITP). The invention provides for genetically engineered expression vectors and host cells comprising the nucleic acid sequence encoding HITP. The invention also provides for the production and use of substantially purified HITP in pharmaceutical compositions to force differentiation and to stop cell division in cancerous cells. The invention also describes diagnostic assays which utilize the polynucleotide to hybridize with the transcripts encoding HITP and the anti-HITP antibodies which specifically bind to HITP.

7 Claims, 11 Drawing Sheets

```
                 9              18             27             36             45             54
5' NNT          TCG           ANC           GNT           CCC           NAA           GGA           CGC           GTG           GGC           GGC           ACG           CGT           GGG           CGA           GAA           GCA           AGC 63             72             81             90             99            108
   TGT          CTC           CAT           CTT           GTC           TGT           ATC           CGC           TGT           TCT           TGT           GAC           GTT           GTG           GAG           ATG           GGG           AGC
                                                                                                                                                                                                    M             G             S 117            126            135            144            153            162
   GTC          CTG           GGG           CTG           TGC           TCC           ATG           GCG           AGC           TGG           ATA           CCA           TGT           TTG           TGT           GGA           AGT           GCC
   V            L             G             L             C             S             M             A             S             W             I             P             C             L             C             G             S             A 171            180            189            198            207            216
   CCG          TGT           TTG           CTA           TGC           CGA           TGC           TGT           CCT           AGT           GGA           AAC           AAC           TCC           ACT           GTA           ACT           AGA
   P            C             L             L             C             R             C             C             P             S             G             N             N             S             T             V             T             R 225            234            243            252            261            270
   TTG          ATC           TAT           GCA           CTT           TTC           TTG           CTT           GTT           GGA           GTA           TGT           GGA           GCT           TGT           GTA           ATG           TTG
   L            I             Y             A             L             F             L             L             V             G             V             C             G             A             C             V             M             L 279            288            297            306            315            324
   ATA          CCA           GGA           ATG           GAA           GAA           CAA           CTG           AAT           AAG           ATT           CCT           GGA           TTT           TGT           GAG           AAT           GAA
   I            P             G             M             E             E             Q             L             N             K             I             P             G             F             C             E             N             E 333            342            351            360            369            378
   AAA          ATG           GAA           GAA           GGG           AAC           TCG           AGA           TGT           TGG           TAT           GCA           GCC           TTG           TTA           TCA           GCT           ACA
   K            M             E             E             G             N             S             R             C             W             Y             A             A             L             L             S             A             T
```

FIGURE 1A

```
    387      396      405      414      423      432
GCT CTG AAT TAT CTG TCT TTA GTT GCT ATC GTC CTG TTC TTT GTC TAC TAC
 A   L   N   Y   L   S   L   V   A   I   V   L   F   F   V   Y   Y 441      450      459      468      477      486
ACT CAT CCA GCC AGT TGT TCA GAA AAC AAG GCG TTC ATC AGT GTC AAC ATG CTC
 T   H   P   A   S   C   S   E   N   K   A   F   I   S   V   N   M   L 495      504      513      522      531      540
CTC TGC GTT GGT GCT ATG TCT GTA ATG TCT ATA CTG CCA AAA ATC CAA GAA TCA CAA
 L   C   V   G   A   M   S   V   M   S   I   L   P   K   I   Q   E   S   Q 549      558      567      576      585      594
CCA AGA TCT GGT TTG TTA CAG TCT TCA GTA ATT ACA GTC TAC ACA ATG TAT TTG
 P   R   S   G   L   L   Q   S   S   V   I   T   V   Y   T   M   Y   L 603      612      621      630      639      648
ACA TGG TCA GCT ATG ACC AAT GAA CCA GAA ACA AAT TGC AAC CCA AGT CTA CTA
 T   W   S   A   M   T   N   E   P   E   T   N   C   N   P   S   L   L 657      666      675      684      693      702
AGC ATA ATT GGC TAC AAT ACA ACA AGC ACT GTC CCA AAG GAA GGG CAG TCA GTC
 S   I   I   G   Y   N   T   T   S   T   V   P   K   E   G   Q   S   V 711      720      729      738      747      756
CAG TGG TGG CAT GCT CAA GGA ATT ATA GGA CTA ATT CTC TTT TTG TTG TGT GTA
 Q   W   W   H   A   Q   G   I   I   G   L   I   L   F   L   L   C   V
```

FIGURE 1B

```
       765         774         783         792         801         810
TTT TAT TCC AGC ATC CGT ACT TCA AAC AAT AGT CAG GTT AAT AAA CTG ACT CTA
 F   Y   S   S   I   R   T   S   N   N   S   Q   V   N   K   L   T   L 819         828         837         846         855         864
ACA AGT GAT GAA TCT ACA TTA ATA GAA GAT GGA GCT AGA AGT GAT GGA TCA
 T   S   D   E   S   T   L   I   E   D   G   A   R   S   D   G   S 873         882         891         900         909         918
CTG GAG GAT GGG GAC GAT GTT CAC CGA GCT GTA GAT AAT GAA AGG GAT GGT GTC
 L   E   D   G   D   D   V   H   R   A   V   D   N   E   R   D   G   V 927         936         945         954         963         972
ACT TAC AGT TAT TCC TTC TTT CAC TTC ATG CTK TTC CTG GCT TCA CTT TAT ATC
 T   Y   S   Y   S   F   F   H   F   M   L   F   L   A   S   L   Y   I 981         990         999        1008        1017        1026
ATG ATG ACC CTT ACC AAC TGG TAC AGG TAT GAA CCC TCT CGT GAG ATG AAA AGT
 M   M   T   L   T   N   W   Y   R   Y   E   P   S   R   E   M   K   S 1035        1044        1053        1062        1071        1080
CAG TGG ACA GCT GTC TGG GTG AAA ATC TCT TCC AGT TGG ATT GGC ATC GTG CTG
 Q   W   T   A   V   W   V   K   I   S   S   S   W   I   G   I   V   L 1089        1098        1107        1116        1125        1134
TAT GTT TGG ACA CTC GTG GCA CCA CTT CTT GTT CTT ACA AAT CGT GAT TTT GAC TGA
 Y   V   W   T   L   V   A   P   L   L   V   L   T   N   R   D   F   D
```

FIGURE 1C

```
     1143           1152           1161           1170           1179           1188
GTG AGA CTT CTA GCA TGA AAG TCC CAC TTT GAT TAT TGC TTA TTT GAA AAC AGT 1197           1206           1215           1224           1233           1242
ATT CCC AAC TTT TGT AAA GTT GTG TAT GTT TTT GCT TCC CAT GTA ACT TCT CCA 1251           1260           1269           1278           1287           1296
GTG TTC TGG CAT GAA TTA GAT TTT ACT GCT TGT CAT TTT GTT ATT TTC TTA CCA 1305           1314           1323           1332           1341           1350
AGT GCA TTG ATA TGT GAA GTA GAA TGA ATT GCA GAG GAA AGT TTT ATG AAT ATG 1359           1368           1377           1386           1395           1404
GTG ATG AGT TAG TAA AAG TGG CCA TTA TTG GGC TTA TTC TCT GCT CTA TAG TTG 1413           1422           1431           1440           1449           1458
TGA AAT GAA GAG TAA AAA CAA ATT TGT TTG ACT ATT TTA AAA TTA TAT TAG ACC 1467           1476           1485           1494           1503           1512
TAA GCT GTT TTA GCA AGC ATT AAA GCA AAT GTA TGG CTG YCT TTG AAT ATT TGA 1521           1530           1539           1548           1557           1566
TGT GTT GCC TGG CAG GAT ACT GCA AAG ANC ATG GTT TAT TTT AAA TTW TAA GAA

1575
GTC ATT TGC AGT  3'
```

```
259  GDDVHR AVDNER DGVTYSYSFFHMLFLASLYIMMTLTNW    530522.aa
388  GQPRRLWTTRKRECSIATLIPPHALL--GFLVHHDDPDQ       GI 1293563
308  GQPRRA-VDNEKEGVQYSYSFFHLMLCCASLYIMMTITSW      GI 459890
371  VKEGPRVIYDEKKGTVYSYSYFHFVLLASLYVMMTLTSW       GI 310100

299  YRYEPS-REM--KSQWTAVWVKISSSWIGIVLY---VW-T      530522.aa
425  LVHPAKFQSM--TSKWPAVWVKISSSWVCLLLYAGPLWLH      GI 1293563
347  YSPDAKFQKV--SSKWLAVWFKMGSSWLCLLLY---LW-T      GI 459890
411  FHYENATIETFFVGSWSIFWVKMASCWMCVLLY---LW-T      GI 310100

332  LVAP------------LVLTNRDFD                     530522.aa
463  LSSPVGTSAEPLSAKDTMELTKVSFTENPYTF              GI 1293563
381  LVAP------------LVLTGRDFS                     GI 459890
447  LVAPLCCPS-------------RQFSV                   GI 310100
```

FIGURE 2C

```
                  10        20        30        40        50        60        70
          MGSVLGLCSMASWIPCLCGSAPCLLCRCCPSGNNSTVTRLIYALFLLVGVCVACVMLIPGMEEQLNKIPG
HELIX                                           hhhhhhhhhhhhhhhhhhhhhhhH
SHEET     SSSSSSSSSSSSSSs    SSSsss                                       TTTT
TURN                    TTTT           TTTTTTTTT
COIL                       C 80        90       100       110       120       130       140
          FCENEKMEEGNSRCWYAALLSATALNYLLSLVAIVLFFVYYTHPASCSENKAFISVNMLLCVGASVMSIL
HELIX      HHHHHHh       hhhhhhhhhhhhhhhhhhhhhH               hHhhhhhhhhhhhhhhh
SHEET     SS         sSSSSSSSSSSSSSSSSSSS        SSSS           SSSSSSSSSSSSSSSSS
TURN             TTTTTT                              TTTTTTTT
COIL 150       160       170       180       190       200       210
          PKIQESQPRSGLLQSSVITVYTMYLTWSAMTNEPETNCNPSLLSIIGYNTTSTVPKEGQSVQWWHAQGII
HELIX     hhhhhhhh     hhhhhH              hhhhhhH                   hhhhhhhhhhhh
SHEET     SSSSSSs   ssssssSSSSSSSSSS            sSSSSSSss  ssSS          SSSSSSSSSS
TURN             TTTTTTTTT                TTTTTTT        TTTTT  TTTT
COIL                                                                CCC
```

FIGURE 5A

```
              220       230       240       250       260       270       280
       GLILFLLCVFYSSIRTSNNSQVNKLTLTSDESTLIEDGGARSDGSLEDGDDVHRAVDNERDGVTYSYSFF
HELIX  hhhhhhhhH                                           hHHHh           hh
SHEET  SSSSSSSSSsSSSS        sSSSSSSs       sSS                           sSssssSS
TURN                TTTTTT        TTTTT        TTTTTTTTTTTTTTTT  TTTTTTTT TTTT
COIL 290       300       310       320       330       340
       HFMLFLASLYIMMTLTNWYRYEPSREMKSQWTAVWVKISSSWIGIVLYVWTLVAPLVLTNRDFD
HELIX  hhhhhhhhhhhH         hhhhhhhhhhhh       hhhhhhhhhhH
SHEET  SSSSSSSSSSSSsSSSSSSS         SSSSSSSSSSS        sSSSSSSSSSSsSSSSS
TURN                  TTTTT              TTTTT                      TTTT
COIL                                                                    C
```

FIGURE 5B

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 344 amino acids
( B ) TYPE: amino acid
( C ) STRANDEDNESS: single
( D ) TOPOLOGY: linear ( i i ) MOLECULE TYPE: peptide ( v i i ) IMMEDIATE SOURCE:
( A ) LIBRARY: BRAIN0T03
( B ) CLONE: 530522

( x i ) SEQUENCE DESCRIPTION: SEQ ID NO:1:

Met Gly Ser Val Leu Gly Leu Cys Ser Met Ala Ser Trp Ile Pro Cys

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |
| Leu | Cys | Gly | Ser | Ala | Pro | Cys | Leu | Leu | Cys | Arg | Cys | Cys | Pro | Ser | Gly |
|   |   |   | 20 |   |   |   |   | 25 |   |   |   |   | 30 |   |   |
| Asn | Asn | Ser | Thr | Val | Thr | Arg | Leu | Ile | Tyr | Ala | Leu | Phe | Leu | Leu | Val |
|   |   |   | 35 |   |   |   | 40 |   |   |   |   | 45 |   |   |   |
| Gly | Val | Cys | Val | Ala | Cys | Val | Met | Leu | Ile | Pro | Gly | Met | Glu | Glu | Gln |
|   |   | 50 |   |   |   |   | 55 |   |   |   | 60 |   |   |   |   |
| Leu | Asn | Lys | Ile | Pro | Gly | Phe | Cys | Glu | Asn | Glu | Lys | Met | Glu | Glu | Gly |
| 65 |   |   |   |   | 70 |   |   |   |   | 75 |   |   |   |   | 80 |
| Asn | Ser | Arg | Cys | Trp | Tyr | Ala | Ala | Leu | Leu | Ser | Ala | Thr | Ala | Leu | Asn |
|   |   |   |   | 85 |   |   |   |   | 90 |   |   |   |   | 95 |   |
| Tyr | Leu | Leu | Ser | Leu | Val | Ala | Ile | Val | Leu | Phe | Phe | Val | Tyr | Tyr | Thr |
|   |   |   | 100 |   |   |   |   | 105 |   |   |   |   | 110 |   |   |
| His | Pro | Ala | Ser | Cys | Ser | Glu | Asn | Lys | Ala | Phe | Ile | Ser | Val | Asn | Met |
|   |   |   | 115 |   |   |   |   | 120 |   |   |   |   | 125 |   |   |
| Leu | Leu | Cys | Val | Gly | Ala | Ser | Val | Met | Ser | Ile | Leu | Pro | Lys | Ile | Gln |
|   |   | 130 |   |   |   |   | 135 |   |   |   |   | 140 |   |   |   |
| Glu | Ser | Gln | Pro | Arg | Ser | Gly | Leu | Leu | Gln | Ser | Ser | Val | Ile | Thr | Val |
| 145 |   |   |   |   | 150 |   |   |   |   | 155 |   |   |   |   | 160 |
| Tyr | Thr | Met | Tyr | Leu | Thr | Trp | Ser | Ala | Met | Thr | Asn | Glu | Pro | Glu | Thr |
|   |   |   |   | 165 |   |   |   |   | 170 |   |   |   |   | 175 |   |
| Asn | Cys | Asn | Pro | Ser | Leu | Leu | Ser | Ile | Ile | Gly | Tyr | Asn | Thr | Thr | Ser |
|   |   |   | 180 |   |   |   |   | 185 |   |   |   |   | 190 |   |   |
| Thr | Val | Pro | Lys | Glu | Gly | Gln | Ser | Val | Gln | Trp | Trp | His | Ala | Gln | Gly |
|   |   |   | 195 |   |   |   |   | 200 |   |   |   |   | 205 |   |   |
| Ile | Ile | Gly | Leu | Ile | Leu | Phe | Leu | Leu | Cys | Val | Phe | Tyr | Ser | Ser | Ile |
|   |   | 210 |   |   |   |   | 215 |   |   |   |   | 220 |   |   |   |
| Arg | Thr | Ser | Asn | Asn | Ser | Gln | Val | Asn | Lys | Leu | Thr | Leu | Thr | Ser | Asp |
| 225 |   |   |   |   | 230 |   |   |   |   | 235 |   |   |   |   | 240 |
| Glu | Ser | Thr | Leu | Ile | Glu | Asp | Gly | Gly | Ala | Arg | Ser | Asp | Gly | Ser | Leu |
|   |   |   |   | 245 |   |   |   |   | 250 |   |   |   |   | 255 |   |
| Glu | Asp | Gly | Asp | Asp | Val | His | Arg | Ala | Val | Asp | Asn | Glu | Arg | Asp | Gly |
|   |   |   | 260 |   |   |   |   | 265 |   |   |   |   | 270 |   |   |
| Val | Thr | Tyr | Ser | Tyr | Ser | Phe | Phe | His | Phe | Met | Leu | Phe | Leu | Ala | Ser |
|   |   | 275 |   |   |   |   | 280 |   |   |   |   | 285 |   |   |   |
| Leu | Tyr | Ile | Met | Met | Thr | Leu | Thr | Asn | Trp | Tyr | Arg | Tyr | Glu | Pro | Ser |
|   |   | 290 |   |   |   |   | 295 |   |   |   |   | 300 |   |   |   |
| Arg | Glu | Met | Lys | Ser | Gln | Trp | Thr | Ala | Val | Trp | Val | Lys | Ile | Ser | Ser |
| 305 |   |   |   |   | 310 |   |   |   |   | 315 |   |   |   |   | 320 |
| Ser | Trp | Ile | Gly | Ile | Val | Leu | Tyr | Val | Trp | Thr | Leu | Val | Ala | Pro | Leu |
|   |   |   |   | 325 |   |   |   |   | 330 |   |   |   |   | 335 |   |
| Val | Leu | Thr | Asn | Arg | Asp | Phe | Asp |   |   |   |   |   |   |   |   |
|   |   |   | 340 |   |   |   |   |   |   |   |   |   |   |   |   |

( 2 ) INFORMATION FOR SEQ ID NO:2:

( i ) SEQUENCE CHARACTERISTICS:
        ( A ) LENGTH: 1576 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( A ) LIBRARY: BRAIN0T03
        ( B ) CLONE: 530522

( x i ) SEQUENCE DESCRIPTION: SEQ ID NO:2:

| | | | | | |
|---|---|---|---|---|---|
| TTCGANCGNT | CCCNAAGGAC | GCGTGGGCGG | CACGCGTGGG | CGAGAAGCAA | GCTGTCTCCA | 60 |
| TCTTGTCTGT | ATCCGCTGCT | CTTGTGACGT | TGTGGAGATG | GGGAGCGTCC | TGGGGCTGTG | 120 |
| CTCCATGGCG | AGCTGGATAC | CATGTTTGTG | TGGAAGTGCC | CCGTGTTTGC | TATGCCGATG | 180 |
| CTGTCCTAGT | GGAAACAACT | CCACTGTAAC | TAGATTGATC | TATGCACTTT | TCTTGCTTGT | 240 |
| TGGAGTATGT | GTAGCTTGTG | TAATGTTGAT | ACCAGGAATG | GAAGAACAAC | TGAATAAGAT | 300 |
| TCCTGGATTT | TGTGAGAATG | AAAAAATGGA | AGAAGGGAAC | TCGAGATGTT | GGTATGCAGC | 360 |
| CTTGTTATCA | GCTACAGCTC | TGAATTATCT | GCTGTCTTTA | GTTGCTATCG | TCCTGTTCTT | 420 |
| TGTCTACTAC | ACTCATCCAG | CCAGTTGTTC | AGAAAACAAG | GCGTTCATCA | GTGTCAACAT | 480 |
| GCTCCTCTGC | GTTGGTGCTT | CTGTAATGTC | TATACTGCCA | AAAATCCAAG | AATCACAACC | 540 |
| AAGATCTGGT | TTGTTACAGT | CTTCAGTAAT | TACAGTCTAC | ACAATGTATT | TGACATGGTC | 600 |
| AGCTATGACC | AATGAACCAG | AAACAAATTG | CAACCCAAGT | CTACTAAGCA | TAATTGGCTA | 660 |
| CAATACAACA | AGCACTGTCC | CAAAGGAAGG | GCAGTCAGTC | CAGTGGTGGC | ATGCTCAAGG | 720 |
| AATTATAGGA | CTAATTCTCT | TTTGTTGTG | TGTATTTAT | TCCAGCATCC | GTACTTCAAA | 780 |
| CAATAGTCAG | GTTAATAAAC | TGACTCTAAC | AAGTGATGAA | TCTACATTAA | TAGAAGATGG | 840 |
| TGGAGCTAGA | AGTGATGGAT | CACTGGAGGA | TGGGGACGAT | GTTCACCGAG | CTGTAGATAA | 900 |
| TGAAAGGGAT | GGTGTCACTT | ACAGTTATTC | CTTCTTTCAC | TTCATGCTKT | TCCTGGCTTC | 960 |
| ACTTTATATC | ATGATGACCC | TTACCAACTG | GTACAGGTAT | GAACCCTCTC | GTGAGATGAA | 1020 |
| AAGTCAGTGG | ACAGCTGTCT | GGGTGAAAAT | CTCTTCCAGT | TGGATTGGCA | TCGTGCTGTA | 1080 |
| TGTTTGGACA | CTCGTGGCAC | CACTTGTTCT | TACAAATCGT | GATTTGACT | GAGTGAGACT | 1140 |
| TCTAGCATGA | AAGTCCCACT | TTGATTATTG | CTTATTTGAA | AACAGTATTC | CCAACTTTTG | 1200 |
| TAAAGTTGTG | TATGTTTTTG | CTTCCCATGT | AACTTCTCCA | GTGTTCTGGC | ATGAATTAGA | 1260 |
| TTTTACTGCT | TGTCATTTTG | TTATTTCTT | ACCAAGTGCA | TTGATATGTG | AAGTAGAATG | 1320 |
| AATTGCAGAG | GAAAGTTTTA | TGAATATGGT | GATGAGTTAG | TAAAAGTGGC | CATTATTGGG | 1380 |
| CTTATTCTCT | GCTCTATAGT | TGTGAAATGA | AGAGTAAAAA | CAAATTTGTT | TGACTATTTT | 1440 |
| AAAATTATAT | TAGACCTAAG | CTGTTTTAGC | AAGCATTAAA | GCAAATGTAT | GGCTGYCTTT | 1500 |
| GAATATTTGA | TGTGTTGCCT | GGCAGGATAC | TGCAAAGANC | ATGGTTTATT | TTAAATTWTA | 1560 |
| AGAAGTCATT | TGCAGT | | | | | 1576 |

( 2 ) INFORMATION FOR SEQ ID NO:3:

( i ) SEQUENCE CHARACTERISTICS:
        ( A ) LENGTH: 494 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 1293563

( x i ) SEQUENCE DESCRIPTION: SEQ ID NO:3:

Met Gly Ala Val Leu Gly Val Phe Ser Leu Ala Ser Trp Val Pro Cys
1               5                   10                  15

Leu Cys Ser Gly Ala Ser Cys Leu Leu Cys Ser Cys Cys Pro Asn Ser
            20                  25                  30

Lys Asn Ser Thr Val Thr Arg Leu Ile Tyr Ala Phe Ile Leu Leu Leu

|       |     |     |     | 35  |     |     |     |     |     | 40  |     |     |     |     |     | 45  |     |     |     |
|-------|-----|-----|-----|-----|-----|-----|-----|-----|-----|-----|-----|-----|-----|-----|-----|-----|-----|-----|-----|

Ser Thr Val Val Ser Tyr Ile Met Gln Arg Lys Glu Met Glu Thr Tyr
            50                      55                      60

Leu Lys Lys Ile Pro Gly Phe Cys Glu Gly Gly Phe Lys Ile His Glu
65                      70                      75                      80

Ala Asp Ile Asn Ala Asp Lys Asp Cys Asp Val Leu Val Gly Tyr Lys
                    85                      90                      95

Ala Val Tyr Arg Ile Ser Phe Ala Met Ala Ile Phe Phe Phe Val Phe
            100                     105                     110

Ser Leu Leu Met Phe Lys Val Lys Thr Ser Lys Asp Leu Arg Ala Ala
            115                     120                     125

Val His Asn Gly Phe Trp Phe Phe Lys Ile Ala Ala Leu Ile Gly Ile
            130                     135                     140

Met Val Gly Ser Phe Tyr Ile Pro Gly Gly Tyr Phe Ser Ser Val Trp
145                     150                     155                     160

Phe Val Val Gly Met Ile Gly Ala Ala Leu Phe Ile Leu Ile Gln Leu
                    165                     170                     175

Val Leu Leu Val Asp Phe Ala His Ser Trp Asn Glu Ser Trp Val Asn
            180                     185                     190

Arg Met Glu Glu Gly Asn Pro Arg Leu Trp Tyr Ala Ala Leu Leu Ser
            195                     200                     205

Phe Thr Ser Ala Phe Tyr Ile Leu Ser Ile Ile Cys Val Gly Leu Leu
210                     215                     220

Tyr Thr Tyr Tyr Thr Lys Pro Asp Gly Cys Thr Glu Asn Lys Phe Phe
225                     230                     235                     240

Ile Ser Ile Asn Leu Ile Leu Cys Val Val Ala Ser Ile Ile Ser Ile
            245                     250                     255

His Pro Lys Ile Gln Glu His Gln Pro Arg Ser Gly Leu Leu Gln Ser
            260                     265                     270

Ser Leu Ile Thr Leu Tyr Thr Met Tyr Leu Thr Trp Ser Ala Met Ser
            275                     280                     285

Asn Glu Pro Asp Arg Ser Cys Asn Pro Asn Leu Met Ser Phe Ile Thr
290                     295                     300

Arg Ile Thr Ala Pro Thr Leu Ala Pro Gly Asn Ser Thr Ala Val Val
305                     310                     315                     320

Leu Pro Leu Leu Pro Pro Ser Lys Ser Gly Ser Leu Leu Asp Ser Asp
            325                     330                     335

Asn Phe Ile Gly Leu Phe Val Phe Val Leu Cys Leu Leu Tyr Ser Ser
            340                     345                     350

Ile Arg Thr Ser Thr Asn Ser Gln Val Asp Lys Leu Thr Leu Ser Gly
            355                     360                     365

Ser Asp Ser Val Ile Leu Gly Asp Thr Thr Thr Ser Gly Ala Ser Asp
370                     375                     380

Glu Glu Asp Gly Gln Pro Arg Arg Leu Trp Thr Thr Arg Lys Arg Glu
385                     390                     395                     400

Cys Ser Ile Ala Thr Leu Ile Pro Pro His Ala Leu Leu Gly Phe Leu
                    405                     410                     415

Val His His Asp Asp Pro Asp Gln Leu Val His Pro Ala Lys Phe Gln
            420                     425                     430

Ser Met Thr Ser Lys Trp Pro Ala Val Trp Val Lys Ile Ser Ser Ser
            435                     440                     445

Trp Val Cys Leu Leu Leu Tyr Ala Gly Pro Leu Trp Leu His Leu Ser
450                     455                     460

-continued

| Ser | Pro | Val | Gly | Thr | Ser | Ala | Glu | Pro | Leu | Ser | Ala | Lys | Asp | Thr | Met |
| 465 | | | | 470 | | | | | 475 | | | | | | 480 |

| Glu | Leu | Thr | Lys | Val | Ser | Phe | Thr | Glu | Asn | Pro | Tyr | Thr | Phe |
| | | | | 485 | | | | | 490 | | | | |

( 2 ) INFORMATION FOR SEQ ID NO:4:

( i ) SEQUENCE CHARACTERISTICS:
        ( A ) LENGTH: 393 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( A ) LIBRARY: GenBank
        ( B ) CLONE: 459890

( x i ) SEQUENCE DESCRIPTION: SEQ ID NO:4:

| Met | Val | Asp | Thr | Lys | Ala | Glu | Lys | Asp | Cys | Asp | Val | Leu | Val | Gly | Phe |
| 1 | | | | 5 | | | | | 10 | | | | | 15 | |

| Lys | Ala | Val | Tyr | Arg | Ile | Asn | Phe | Ala | Val | Ala | Ile | Phe | Phe | Phe | Ala |
| | | | | 20 | | | | 25 | | | | | 30 | | |

| Phe | Phe | Leu | Leu | Met | Leu | Lys | Val | Lys | Thr | Ser | Lys | Asp | Pro | Arg | Ala |
| | | | 35 | | | | 40 | | | | | 45 | | | |

| Ala | Val | His | Asn | Gly | Phe | Trp | Phe | Phe | Lys | Ile | Ala | Ala | Ile | Ile | Gly |
| | 50 | | | | | 55 | | | | | | 60 | | | |

| Ile | Met | Ile | Gly | Ser | Phe | Tyr | Ile | Pro | Gly | Gly | Ser | Phe | Thr | Glu | Val |
| 65 | | | | | 70 | | | | | 75 | | | | | 80 |

| Trp | Phe | Val | Ala | Gly | Met | Leu | Gly | Ala | Ser | Phe | Phe | Ile | Ile | Ile | Gln |
| | | | | 85 | | | | | 90 | | | | | 95 | |

| Leu | Val | Leu | Leu | Val | Asp | Met | Ala | His | Ser | Trp | Asn | Glu | Leu | Trp | Val |
| | | | | 100 | | | | | 105 | | | | | 110 | |

| Asn | Arg | Met | Glu | Glu | Gly | Asn | Pro | Arg | Leu | Trp | Tyr | Ala | Ala | Leu | Leu |
| | | | 115 | | | | | 120 | | | | | 125 | | |

| Ser | Phe | Thr | Ser | Leu | Phe | Tyr | Ile | Leu | Ser | Ile | Val | Phe | Ala | Ala | Leu |
| | | 130 | | | | | 135 | | | | | 140 | | | |

| Leu | Tyr | Val | Phe | Tyr | Thr | Lys | Pro | Asp | Asp | Cys | Thr | Glu | Asn | Lys | Val |
| 145 | | | | | 150 | | | | | 155 | | | | | 160 |

| Phe | Ile | Ser | Leu | Asn | Leu | Ile | Phe | Cys | Val | Ala | Val | Ser | Ile | Val | Ser |
| | | | | 165 | | | | | 170 | | | | | 175 | |

| Ile | Leu | Pro | Lys | Val | Gln | Glu | His | Gln | Pro | Arg | Ser | Gly | Leu | Leu | Gln |
| | | | | 180 | | | | | 185 | | | | | 190 | |

| Ser | Ser | Ile | Ile | Thr | Leu | Tyr | Thr | Leu | Tyr | Leu | Thr | Trp | Ser | Ala | Met |
| | | | 195 | | | | | 200 | | | | | 205 | | |

| Thr | Asn | Glu | Pro | Glu | Arg | Ser | Cys | Asn | Pro | Ser | Leu | Met | Ser | Ile | Ile |
| | | 210 | | | | | 215 | | | | | 220 | | | |

| Thr | His | Leu | Thr | Ser | Pro | Thr | Val | Ser | Pro | Ala | Asn | Ser | Thr | Thr | Leu |
| 225 | | | | | 230 | | | | | 235 | | | | | 240 |

| Ala | Pro | Ala | Tyr | Arg | Pro | Pro | Ser | Gln | Ser | Gly | His | Phe | Met | Asn | Leu |
| | | | | 245 | | | | | 250 | | | | | 255 | |

| Asp | Asp | Ile | Trp | Gly | Leu | Ile | Ile | Phe | Val | Phe | Cys | Leu | Ile | Tyr | Ser |
| | | | | 260 | | | | | 265 | | | | | 270 | |

| Ser | Phe | Arg | Thr | Ser | Ser | Asn | Ser | Gln | Val | Asn | Lys | Leu | Thr | Leu | Ser |
| | | 275 | | | | | 280 | | | | | 285 | | | |

| Gly | Ser | Asp | Ser | Val | Ile | Leu | Gly | Asp | Thr | Thr | Asn | Gly | Ala | Asn | Asp |
| | | 290 | | | | | 295 | | | | | 300 | | | |

```
Glu  Glu  Asp  Gly  Gln  Pro  Arg  Arg  Ala  Val  Asp  Asn  Glu  Lys  Glu  Gly
305                      310                 315                      320

Val  Gln  Tyr  Ser  Tyr  Ser  Phe  Phe  His  Leu  Met  Leu  Cys  Cys  Ala  Ser
               325                      330                           335

Leu  Tyr  Ile  Met  Met  Thr  Ile  Thr  Ser  Trp  Tyr  Ser  Pro  Asp  Ala  Lys
               340                      345                      350

Phe  Gln  Lys  Val  Ser  Ser  Lys  Trp  Leu  Ala  Val  Trp  Phe  Lys  Met  Gly
          355                      360                      365

Ser  Ser  Trp  Leu  Cys  Leu  Leu  Leu  Tyr  Leu  Trp  Thr  Leu  Val  Ala  Pro
     370                      375                      380

Leu  Val  Leu  Thr  Gly  Arg  Asp  Phe  Ser
385                      390
```

(2) INFORMATION FOR SEQ ID NO:5:

(i) SEQUENCE CHARACTERISTICS:
        (A) LENGTH: 460 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 310100

(xi) SEQUENCE DESCRIPTION: SEQ ID NO:5:

```
Met  Ser  Ala  Arg  Cys  Cys  Ala  Gly  Gln  Leu  Ala  Cys  Cys  Cys  Gly  Ser
1                   5                        10                      15

Ala  Gly  Cys  Ala  Leu  Cys  Cys  Gly  Cys  Cys  Pro  Lys  Phe  Arg  Gln  Ser
               20                  25                      30

Arg  Ser  Thr  Arg  Phe  Met  Tyr  Leu  Phe  Tyr  Phe  Thr  Leu  Val  Ile  Ile
          35                      40                      45

Pro  Cys  Cys  Val  Met  Met  Ser  Pro  Ser  Val  Met  Lys  Gln  Met  Thr  Glu
     50                      55                      60

His  Ile  Pro  Phe  Phe  Glu  Asp  Phe  Cys  Lys  Gly  Ile  Lys  Ala  Gly  Asp
65                       70                      75                      80

Thr  Cys  Glu  Asn  Leu  Val  Gly  Tyr  Ser  Ala  Val  Tyr  Arg  Val  Cys  Phe
               85                      90                      95

Gly  Met  Ala  Cys  Phe  Phe  Val  Phe  Cys  Val  Leu  Thr  Phe  Lys  Val
               100                     105                     110

Asn  Asn  Ser  Lys  Ser  Cys  Arg  Ala  Ser  Ile  His  Asn  Gly  Phe  Trp  Phe
          115                     120                     125

Phe  Lys  Leu  Leu  Leu  Leu  Gly  Ala  Met  Cys  Ser  Gly  Ala  Phe  Phe  Ile
     130                     135                     140

Pro  Asp  Gln  Glu  Thr  Phe  Leu  Asn  Val  Trp  Arg  Tyr  Val  Gly  Ala  Val
145                     150                     155                     160

Gly  Ser  Phe  Phe  Phe  Ile  Cys  Ile  Gln  Leu  Leu  Leu  Ile  Val  Glu  Phe
               165                     170                     175

Ala  His  Lys  Trp  Asn  Lys  Asn  Trp  Thr  Ala  Gly  Thr  Val  Arg  Asn  Lys
               180                     185                     190

Leu  Trp  Tyr  Ala  Ser  Leu  Ser  Leu  Ala  Leu  Ile  Met  Tyr  Ser  Ile  Ala
          195                     200                     205

Val  Gly  Gly  Leu  Ala  Leu  Met  Ala  Val  Phe  Tyr  Thr  Gln  Trp  Asp  Asp
     210                     215                     220

Cys  Met  Asp  Asn  Lys  Ile  Leu  Leu  Gly  Val  His  Gly  Gly  Leu  Cys  Val
225                     230                     235                     240
```

| | | | | | | | | | | | | | | |
|---|---|---|---|---|---|---|---|---|---|---|---|---|---|---|
| Leu | Ile | Ser | Leu | Ala 245 | Ala | Ile | Ser | Pro | Cys 250 | Val | Gln | Asn | Arg | Gln 255 | Pro |
| His | Ser | Gly | Leu 260 | Leu | Gln | Pro | Gly | Leu 265 | Ile | Ser | Cys | Tyr | Val 270 | Thr | Tyr |
| Leu | Thr | Phe 275 | Ser | Ala | Leu | Thr | Ser 280 | Lys | Pro | Glu | Lys | Val 285 | Val | Lys | Asp |
| Glu | His 290 | Gly | Lys | Asn | Val | Thr 295 | Ile | Cys | Val | Pro | Asp 300 | Phe | Gly | Gln | Asp |
| Phe 305 | Arg | Arg | Asp | Glu | Ser 310 | Met | Val | Thr | Trp | Leu 315 | Gly | Thr | Leu | Leu | Leu 320 |
| Val | Val | Cys | Ile | Ser 325 | Tyr | Ser | Cys | Leu | Thr 330 | Ser | Thr | Thr | Arg | Ser 335 | Ser |
| Ser | Asp | Ala | Leu 340 | Gln | Arg | Arg | Tyr | Gly 345 | Ala | Pro | Glu | Leu | Glu 350 | Val | Ala |
| Arg | Cys | Cys 355 | Phe | Cys | Phe | Gly | Pro 360 | Asp | Gly | Glu | Asp | Thr 365 | Glu | Glu | Gln |
| Gln | Asn 370 | Val | Lys | Glu | Gly | Pro 375 | Arg | Val | Ile | Tyr | Asp 380 | Glu | Lys | Lys | Gly |
| Thr 385 | Val | Tyr | Ser | Tyr | Ser 390 | Tyr | Phe | His | Phe | Val 395 | Leu | Leu | Leu | Ala | Ser 400 |
| Leu | Tyr | Val | Met | Met 405 | Thr | Leu | Thr | Ser | Trp 410 | Phe | His | Tyr | Glu | Asn 415 | Ala |
| Thr | Ile | Glu | Thr 420 | Phe | Phe | Val | Gly | Ser 425 | Trp | Ser | Ile | Phe | Trp 430 | Val | Lys |
| Met | Ala | Ser 435 | Cys | Trp | Met | Cys | Val 440 | Leu | Leu | Tyr | Leu | Trp 445 | Thr | Leu | Val |
| Ala | Pro 450 | Leu | Cys | Cys | Pro | Ser 455 | Arg | Gln | Phe | Ser | Val 460 | | | | |

HUMAN INDUCED TUMOR PROTEIN

FIELD OF THE INVENTION

The present invention relates to nucleic acid and amino acid sequences of a novel human induced tumor protein which shares features with other proteins involved in cell differentiation and to the use of these sequences in the diagnosis, study, prevention and treatment of disease.

BACKGROUND OF THE INVENTION

Lebel and Mes-Masson (1994 DNA Seq 5:31-39) describe a cDNA derived from MT-PVLT-10 transgenic mice, the males of which develop testicular tumors at advanced ages. The mouse cDNA hybridizes to a 2.6 kilobase mRNA which is expressed in various other tissues including liver, testes, and brain. In immortalized cell lines derived from testicular tumors, the expression of this mRNA is approximately two to fifteen times higher than in similar cell lines derived from pre-adenomatous testes. The mouse cDNA consists of a coding region of 1179 nucleotides which predicts a polypeptide of 393 amino acids with an estimated molecular weight of 44.3 kD.

A developmentally regulated gene, designated TPO-1, has been sequenced by Pfeiffer (1993, unpublished). TPO-1 is related to the induced mouse testicular tumor sequence and is expressed during the transition from oligodendroblast to oligodendrocyte in the telencephalon of newborn Sprague-Dawley rats. The open reading frame, nucleotides 156-1538 within the 5395 bp mRNA, encodes a 459 amino acid polypeptide.

Another related protein, Diff 33, is expressed in trophoblast cells from human placenta (Dakuor J et al (1996) unpublished). The 1746 base mRNA contains an open reading frame, nucleotides 107-1591, which encode a polypeptide of 494 amino acid residues which also has homology to the induced mouse testicular tumor sequence.

Differentiation genes, such as Diff 33, have been described in various animal systems. Vielkind (1976, J Exp Zoology 196:197-204) was one of the first scientists to describe the activity of one of the differentiation genes in platyfish-swordtail melanomas. In this case, the differentiation gene appeared to promote the conversion of melanoma cells to melanocytes. Vieland suggested that the dosage of Diff was important in the genetic control of the cell differentiation process. In 1989, Schwab (IARC Sci Publ 239-54) extended that same concept by reporting that Diff works through genetic suppression of oncogenes by controlling the terminal differentiation of cells. More recently, Raza A et al (1993; Am J Hematol 42:147-57) have described the in vivo expression of Diff in the long term survival of patients of acute myeloid leukemia. They suggest that the ability to monitor Diff expression has both clinical and prognostic significance.

Discovery of new molecules related to or in the Diff gene family is useful for developing diagnostic or therapeutic compositions directed at melanomas and other forms of cancer. The overexpression of the gene in or the ability to supply the protein to cancerous cells has the potential to suppress relevant oncogenes or to force terminal differentiation thereby stopping cell division and growth of the cancerous cells.

SUMMARY

The present invention discloses a novel human induced tumor protein, hereinafter referred to as HITP, which shares features with other proteins involved in cell differentiation. Accordingly, the invention features a substantially purified HITP, as shown in the amino acid sequence of SEQ ID NO:1.

HITP has 344 amino acid residues, a number of which are conserved cysteines—$C_{16}$, $C_{18}$, $C_{23}$, $C_{26}$, $C_{28}$, $C_{29}$, $C_{117}$, $C_{131}$, $C_{178}$, and $C_{218}$. HITP also has potential N glycolysation sites at $N_{33}$, $N_{34}$, $N_{179}$, $N_{189}$, and $N_{228}$ several hydrophobic alpha helices, $L_{40}$-$I_{69}$; $W_{85}$-$V_{109}$; $K_{121}$-$Q_{149}$; $E_{197}$-$F_{220}$; and $F_{279}$-$M_{295}$ which may be membrane spanning regions.

One aspect of the invention features isolated and substantially purified polynucleotides which encode HITP. In a particular aspect, the polynucleotide is the nucleotide sequence of SEQ ID NO:2. In addition, the invention features polynucleotide sequences that hybridize under stringent conditions to SEQ ID NO:2.

The invention further relates to the nucleic acid sequence encoding HITP, oligonucleotides, peptide nucleic acids (PNA), fragments, portions or antisense molecules thereof. The present invention relates, in part, to the inclusion of the nucleic acid sequence encoding HITP in an expression vector which can be used to transform host cells or organisms. The invention also provides therapeutic transformation of cells or tissues involved in the development of melanoma or other cancers, such as those of the brain, breast, and colon.

The present invention also relates to a method for producing HITP or a fragment thereof. It contemplates the delivery of purified HITP, alone or in a pharmaceutically acceptable excipient, to cells or tissues involved in the development of melanoma or other cancers. It also encompasses antibodies which bind specifically to HITP and can be used to diagnose the presence of melanomas or other cancers such as brain, breast, and colon.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of the human induced tumor protein. The alignment was produced using MacDNAsis™ software (Hitachi Software Engineering Co Ltd).

FIGS. 2A, 2B, and 2C shows the amino acid sequence alignments among human induced tumor protein (SEQ ID NO:1), GI 1293563 (SEQ ID NO:3; Dakuor and Morrish, supra), GI 459890 (SEQ ID NO:4; Lebel and Mes-Masson, supra), and GI 310100 (SEQ ID NO: 5; Pfeiffer, supra). These alignments were produced using the multisequence alignment program of DNAStar™ software (DNAStar Inc, Madison Wis.).

FIGS. 5A and 5B shows the secondary structure for the human induced tumor protein, SEQ ID NO:1, generated using MacDNAsis software.

DESCRIPTION OF THE INVENTION

Definitions

Figure 3:
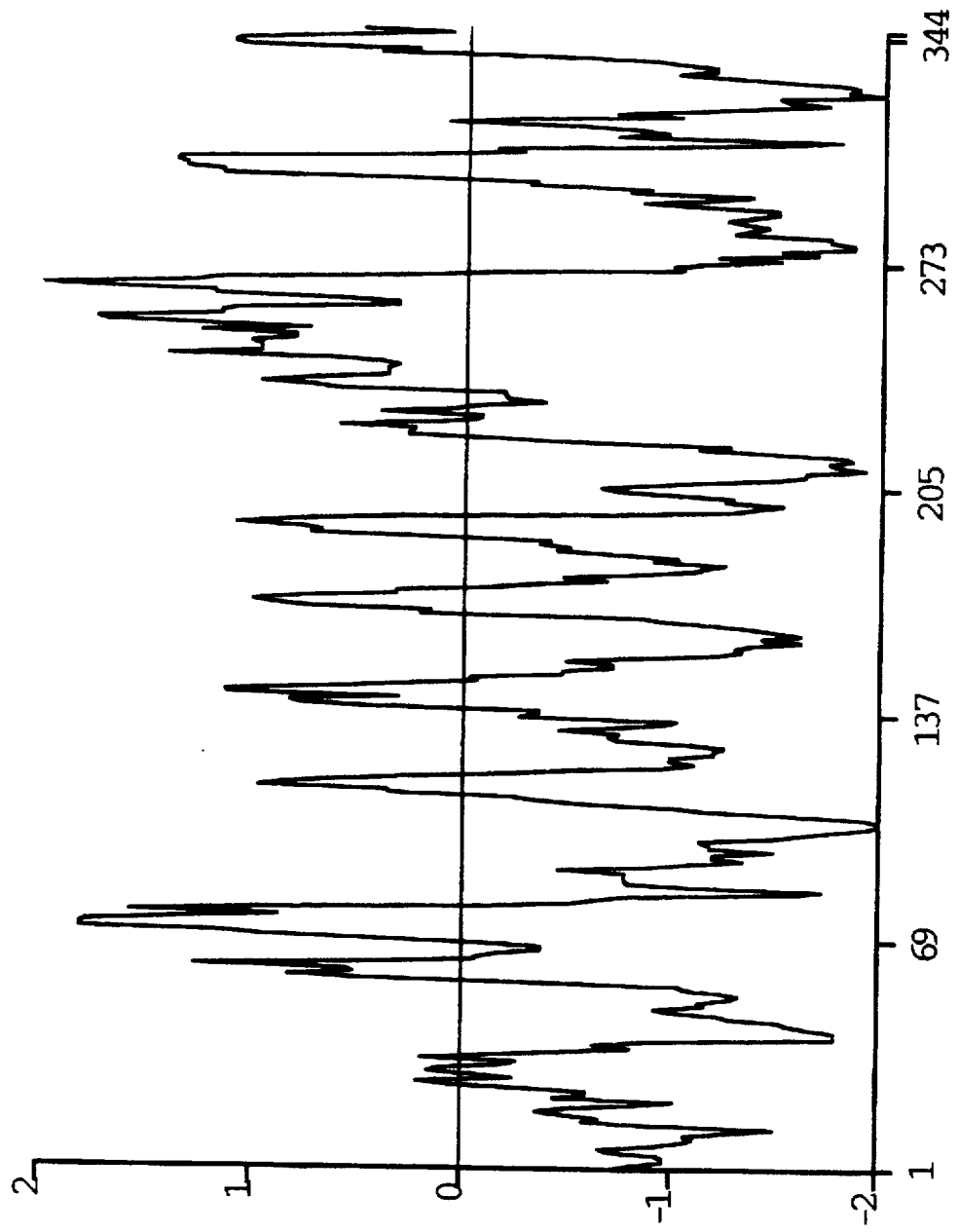
FIG. 3 shows the hydrophobicity plot for human induced tumor protein, SEQ ID NO:1, generated using MacDNAsis software; the X axis reflects amino acid position, and the negative Y axis, hydrophobicity.

"Nucleic acid sequence" as used herein refers to an oligonucleotide, nucleotide or polynucleotide, and fragments or portions thereof, and to DNA or RNA of genomic or synthetic origin which may be single- or double-stranded, and represents the sense or antisense strand. Similarly, amino acid sequence as used herein refers to peptide or protein sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen PE et al (1993) Anticancer Drug Des 8:53–63).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring HITP.

A "substitution" results from the replacement of one or more nucleotides or amino acids by different nucleotides or amino acids, respectively.

As used herein, HITP refers to the amino acid sequence of substantially purified HITP obtained from any species, particularly mammalian, including bovine, ovine, porcine, murine, equine, and preferably human, from any source whether natural, synthetic, semi-synthetic or recombinant.

A "variant" of HITP is defined as an amino acid sequence that differs by one or more amino acids. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNAStar software.

The term "biologically active" refers to a HITP having structural, regulatory or biochemical functions of a naturally occurring HITP. Likewise, "immunologically active" defines the capability of the natural, recombinant or synthetic HITP, or any oligopeptide thereof, to induce a specific immune response in appropriate animals or cells and to bind with specific antibodies.

The term "derivative" as used herein refers to the chemical modification of a nucleic acid encoding HITP or the encoded HITP. Illustrative of such modifications would be replacement of hydrogen by an alkyl, acyl, or amino group. A nucleic acid derivative would encode a polypeptide which retains essential biological characteristics of natural HITP.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification is defined as the production of additional copies of a nucleic acid sequence and is generally carried out using polymerase chain reaction technologies well known in the art (Dieffenbach CW and GS Dveksler (1995) *PCR Primer, a Laboratory Manual*, Cold Spring Harbor Press, Plainview N.Y.).

"Stringency" typically occurs in a range from about Tm-5° C. (5° C. below the Tm of the probe)to about 20° C. to 25° C. below Tm. As will be understood by those of skill in the art, a stringency hybridization can be used to identify or detect identical polynucleotide sequences or to identify or detect similar or related polynucleotide sequences.

Description

The present invention relates to a novel human induced tumor protein which was initially identified among the partial cDNAs from a brain library (BRAINOT03) and to the use of the disclosed nucleic acid and amino acid sequences in the study, diagnosis, prevention and treatment of disease.

Figure 2A:
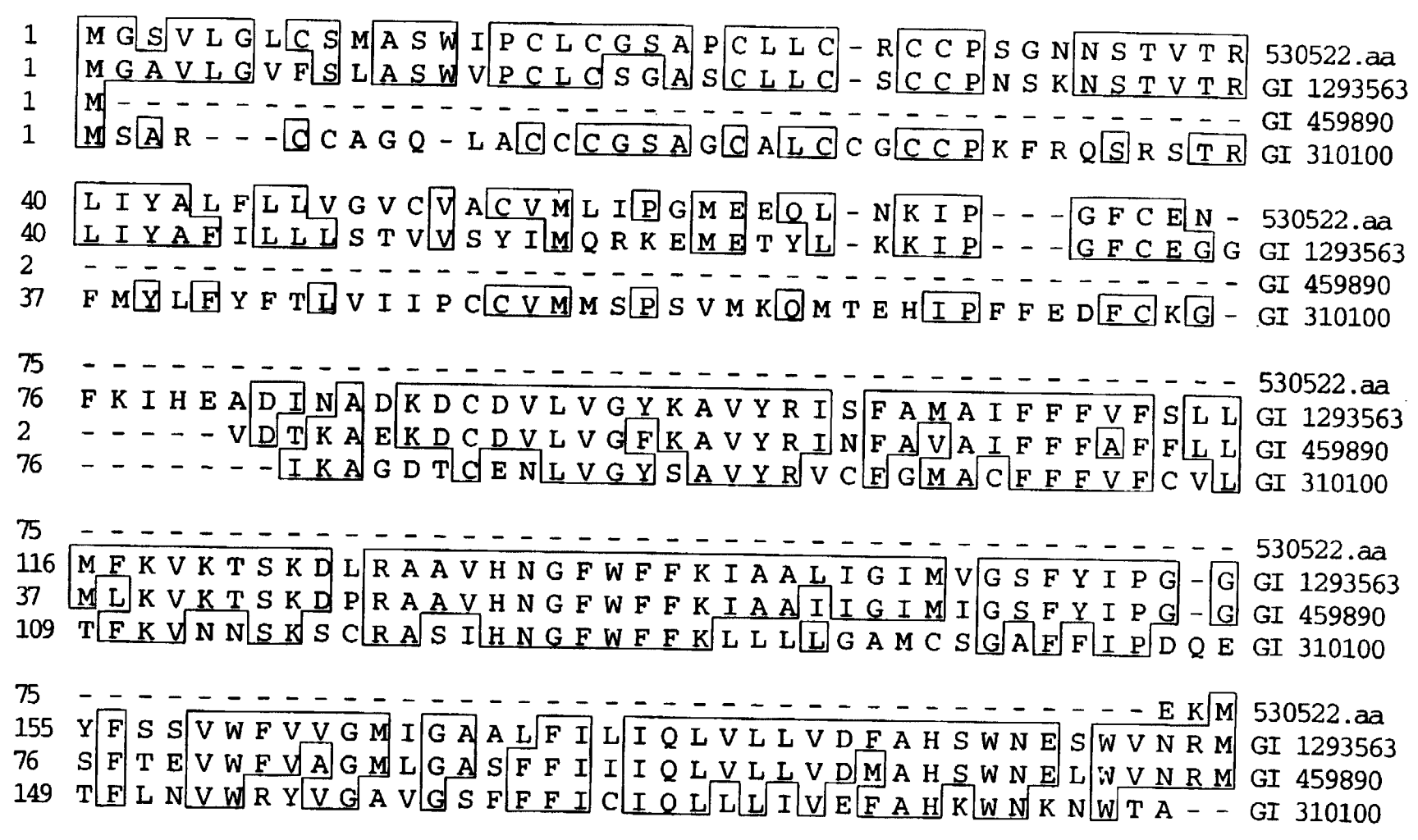
Figure 2B:
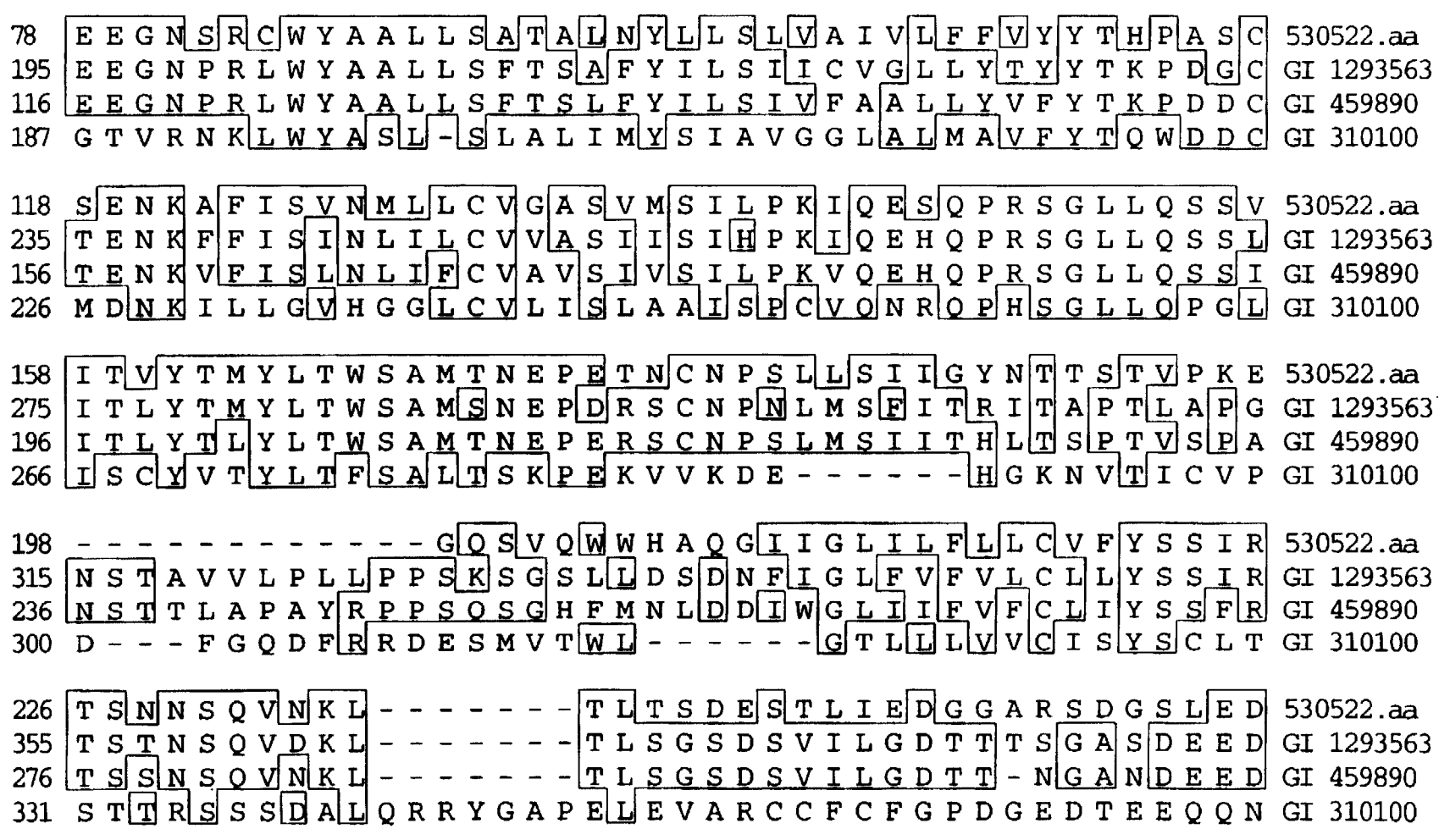

The nucleic acid sequence encoding a portion of the novel membrane associated protein was identified in Incyte Clone 530522 through a computer-generated search for amino acid sequence alignments. The nucleic acid sequence, SEQ ID NO:2, disclosed herein, encodes the amino acid sequence, SEQ ID NO:1, designated in upper case, HITP (FIG. 2). The full length cDNA was assembled from Incyte Clones 104067H1 (BMARNOT02); 115131H1 (TESTNOT01); 397536H1 (PITUNOT02); 515420H1 (MMLR1DT01); 530522CB1, 530522H1, 530522X11, 530522X12, 530522X13, 530522X14 530522X15, and 530522X16 (BRAINOT03); 624681H1 (PGANNOT01); 870277H1 and 877324H1 (LUNGAST01); 894332H1 (BRSTNOT05); 904362H1 (COLNNOT07); 908540H1 (COLNNOT09); and 93908H1 (HYPONOB01) from the LIFESEQ™ database (Incyte Pharmaceuticals, Palo Alto, Calif.)

Figure 4:
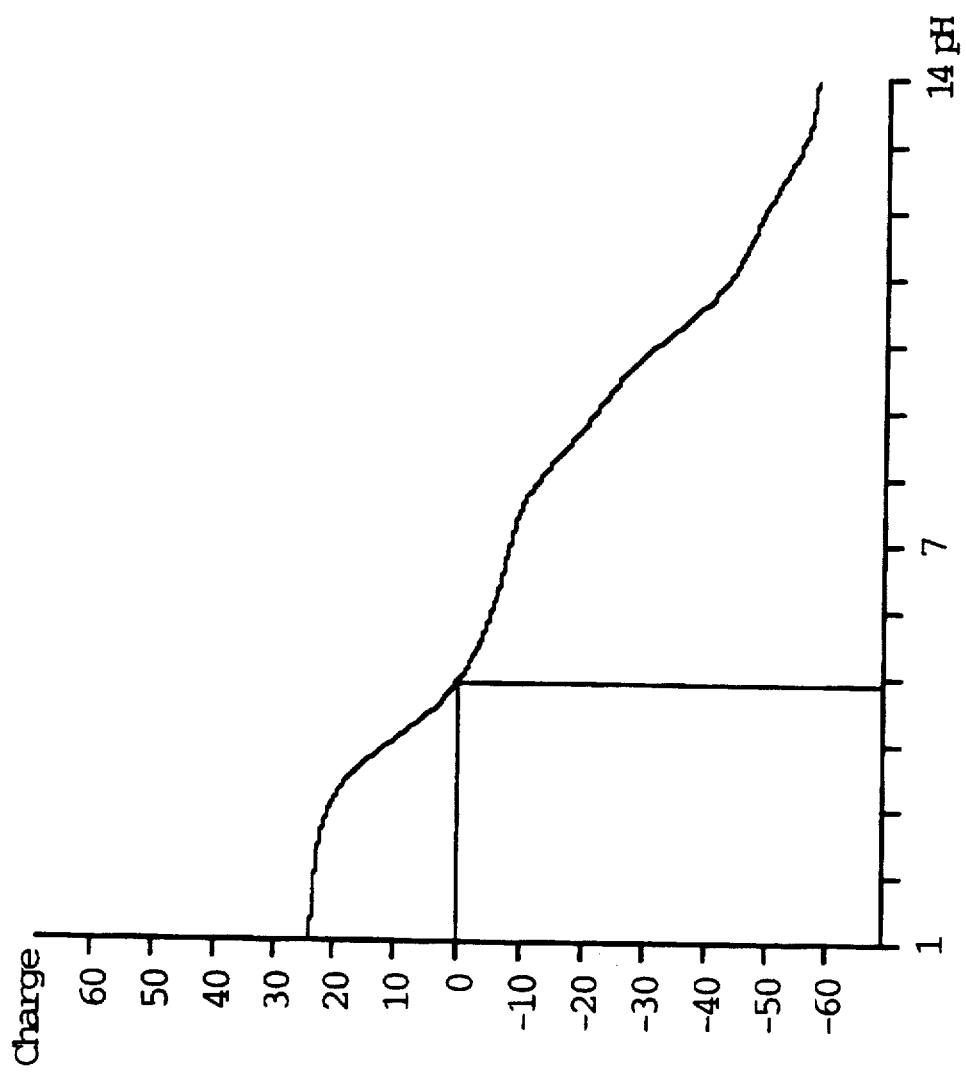
FIG. 4 shows the isoelectric plot for human induced tumor protein, SEQ ID NO:1, generated using MacDNAsis software.

HITP has a number of conserved cysteines ($C_{16}$, $C_{18}$, $C_{23}$, $C_{26}$, $C_{28}$, $C_{29}$, $C_{117}$, $C_{131}$, $C_{178}$, and $C_{218}$), five potential N glycolysation sites ($N_{33}$, $N_{34}$, $N_{179}$, $N_{189}$, and $N_{228}$), and several hydrophobic alpha helices ($L_{40}$-$I_{69}$; $W_{85}$-$V_{109}$; $K_{121}$-$Q_{149}$; $E_{197}$-$F_{220}$; and $F_{279}$-$M_{295}$) which may be membrane spanning regions. HITP is missing a region of 116 residues between $N_{71}$ and $E_{75}$ which are common to the Diff33 gene from human placenta (GI 459890), mouse testicular tumor protein (GI 459890,), and the rat developmentally regulated protein (GI 310100). In all other regions, however, HITP has 50% amino acid identity with the consensus sequence run for all four molecules shown in FIG. 3. The hydrophobicity plot, isoelectric plot and secondary structure for HITP are shown in FIGS. 4–6.

The HITP Coding Sequences

The nucleic acid and deduced amino acid sequences of HITP are shown in FIG. 1. In accordance with the invention, any nucleic acid sequence which encodes HITP can be used to generate recombinant molecules which express HITP. In a specific embodiment described herein, a partial sequence encoding HITP was first isolated as Incyte Clone 530522 from a macrophage cDNA library (BRAINOT03).

It will be appreciated by those skilled in the art that as a result of the degeneracy of the genetic code, a multitude of HITP-encoding nucleotide sequences, some bearing minimal homology to the nucleotide sequences of any known and naturally occurring gene may be produced. The invention contemplates each and every possible variation of nucleotide sequence that could be made by selecting combinations based on possible codon choices. These combinations are made in accordance with the standard triplet genetic code as applied to the nucleotide sequence encoding naturally occurring HTTP, and all such variations are to be considered as being specifically disclosed.

Although nucleotide sequences which encode HTTP and its variants are preferably capable of hybridizing to the nucleotide sequence of the naturally occurring sequence under appropriately selected conditions of stringency, it may be advantageous to produce nucleotide sequences encoding HTTP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HTTP and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding HTTP and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a sequence encoding HTTP or any portion thereof.

Also included within the scope of the present invention are polynucleotide sequences that are capable of hybridizing to the nucleotide sequence of FIGS. 1A and 1B under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and may be used at a defined "stringency".

Altered nucleic acid sequences encoding HTTP which may be used in accordance with the invention include deletions, insertions or substitutions of different nucleotides resulting in a polynucleotide that encodes the same or a functionally equivalent HTTP. The protein may also show deletions, insertions or substitutions of amino acid residues which produce a silent change and result in a functionally equivalent HTTP. Deliberate amino acid substitutions may be made on the basis of similarity in polarity, charge, solubility, hydrophobicity, hydrophilicity, and/or the amphipathic nature of the residues as long as the biological activity of HTTP is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles encoding HTTP. As used herein, an "allele" or "allelic sequence" is an alternative form of the nucleic acid sequence encoding HTTP. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, Sequenase® (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

Extending the Polynucleotide Sequence

The polynucleotide sequence encoding HTTP may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72°0 C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequence is walking PCR (Parker JD et al (1991) Nucleic Acids Res 19:3055–60), a method for targeted gene walking. Alternatively, PCR, nested primers, PromoterFinder™ (Clontech, Palo Alto Calif.) and PromoterFinder libraries can be used to walk in genomic DNA. This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze either the size or confirm the nucleotide sequence in sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. Genotyper™ and Sequence Navigator™ from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez MC et al (1993) Anal Chem 65:2851–8).

Expression of the Nucleotide Sequence

In accordance with the present invention, polynucleotide sequences which encode HITP, fragments of the polypeptide, fusion proteins or functional equivalents thereof may be used in recombinant DNA molecules that direct the expression of HITP in appropriate host cells. Due to the inherent degeneracy of the genetic code, other DNA sequences which encode substantially the same or a functionally equivalent amino acid sequence, may be used to clone and express HITP. As will be understood by those of skill in the art, it may be advantageous to produce HITP-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of HITP expression or to produce recombinant RNA transcripts having desirable properties, such as a longer half-life, than transcripts produced from naturally occurring sequence.

The nucleotide sequences of the present invention can be engineered in order to alter a HITP-encoding sequence for a variety of reasons, including but not limited to, alterations which modify the cloning, processing and/or expression of the gene product. For example, mutations may be introduced using techniques which are well known in the art, eg. site-directed mutagenesis to insert new restriction sites, to alter glycosylation patterns, to change codon preference, to produce splice variants, etc.

In another embodiment of the invention, a natural, modified or recombinant HITP-encoding sequence may be ligated to a heterologous sequence to encode a fusion protein. For example, for screening of peptide libraries for inhibitors of HITP activity, it may be useful to encode a chimeric HITP protein that is recognized by a commercially available antibody. A fusion protein may also be engineered to contain a cleavage site located between a HITP and the heterologous protein sequence, so that the HITP may be cleaved and substantially purified away from the heterologous moiety.

In an alternate embodiment of the invention, the sequence encoding HITP may be synthesized, whole or in part, using chemical methods well known in the art (see Caruthers MH et al (1980) Nuc Acids Res Symp Ser 215–23, Horn T et al (1980) Nuc Acids Res Symp Ser 225–32, etc). Alternatively, the protein itself could be produced using chemical methods to synthesize a HITP amino acid sequence, whole or in part. For example, peptide synthesis can be performed using various solid-phase techniques (Roberge JY et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg. Creighton (1983) Proteins, Structures and Molecular Principles, WH Freeman and Co, New York N.Y.). The composition of the synthetic peptides may be confirmed by amino acid analysis or sequencing (eg. the Edman degradation procedure; Creighton, supra). Additionally the amino acid sequence of HITP, or any part thereof, may be altered during direct synthesis and/or combined using chemical methods with sequences from other proteins, or any part thereof, to produce a variant polypeptide.

Expression Systems

In order to express a biologically active HITP, the nucleotide sequence encoding HITP or its functional equivalent, is inserted into an appropriate expression vector, ie. a vector which contains the necessary elements for the transcription and translation of the inserted coding sequence.

Methods which are well known to those skilled in the art can be used to construct expression vectors containing a HITP-encoding sequence and appropriate transcriptional or translational controls. These methods include in vitro recombinant DNA techniques, synthetic techniques and in vivo recombination or genetic recombination. Such techniques are described in Sambrook et al (1989) Molecular Cloning, a Laboratory Manual, Cold Spring Harbor Press, Plainview N.Y. and Ausubel FM et al (1989) Current Protocols in Molecular Biology, John Wiley & Sons, New York N.Y.

A variety of expression vector/host systems may be utilized to contain and express a HITP-encoding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg. baculovirus); plant cell systems transfected with virus expression vectors (eg. cauliflower mosaic virus, CaMV; tobacco mosaic virus, TMV) or transformed with bacterial expression vectors (eg. Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla Calif.) or pSport1 (Gibco BRL) and ptrp-lac hybrids and the like may be used. The baculovirus polyhedrin promoter may be used in insect cells. Promoters or enhancers derived from the genomes of plant cells (eg. heat shock, RUBISCO; and storage protein genes) or from plant viruses (eg. viral promoters or leader sequences) may be cloned into the vector. In mammalian cell systems, promoters from the mammalian genes or from mammalian viruses are most appropriate. If it is necessary to generate a cell line that contains multiple copies of the sequence encoding HITP, vectors based on SV40 or EBV may be used with an appropriate selectable marker.

In bacterial systems, a number of expression vectors may be selected depending upon the use intended for HITP. For example, when large quantities of HTTP are needed for the induction of antibodies, vectors which direct high level expression of fusion proteins that are readily purified may be desirable. Such vectors include, but are not limited to, the multifunctional *E. coli* cloning and expression vectors such as Bluescript® (Stratagene), in which the sequence encoding HTTP may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding HTTP may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi RM (1991) Results Probl Cell Differ 17:85–105) may be used. These constructs can be introduced into plant cells by direct DNA transformation or pathogen-mediated transfection. For reviews of such techniques, see Hobbs S or Murry LE in McGraw Hill *Yearbook of Science and Technology* (1992) McGraw Hill New York N.Y., pp 191–196 or Weissbach and Weissbach (1988) *Methods for Plant Molecular Biology*, Academic Press, New York N.Y., pp 421–463.

An alternative expression system which could be used to express HTTP is an insect system. In one such system, *Autographa californica* nuclear polyhedrosis virus (AcNPV) is used as a vector to express foreign genes in *Spodoptera frugiperda* cells or in Trichoplusia larvae. The sequence encoding HTTP may be cloned into a nonessential region of the virus, such as the polyhedrin gene, and placed under control of the polyhedrin promoter. Successful insertion of the sequence encoding HTTP will render the polyhedrin gene inactive and produce recombinant virus lacking protein coat. The recombinant viruses are then used to infect *S. frugiperda* cells or Trichoplusia larvae in which HTTP is expressed (Smith et al (1983) J Virol 46:584; Engelhard EK et al (1994) Proc Nat Acad Sci 91:3224–7).

In mammalian host cells, a number of viral-based expression systems may be utilized. In cases where an adenovirus is used as an expression vector, a sequence encoding HTTP may be ligated into an adenovirus transcription/translation complex consisting of the late promoter and tripartite leader sequence. Insertion in a nonessential E1 or E3 region of the viral genome will result in a viable virus capable of expressing in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a sequence encoding HTTP. These signals include the ATG initiation codon and adjacent sequences. In cases where the sequence encoding HTTP, its initiation codon and upstream sequences are inserted into the most appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express HTTP may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman SC and RC Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes Calif. et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the sequence encoding HITP is inserted within a marker gene sequence, recombinant cells containing the sequence encoding HITP can be identified by the absence of marker gene function. Alternatively, a marker gene can be placed in tandem with the sequence encoding HITP under the control of a single promoter. Expression of the marker gene in response to induction or selection usually indicates expression of the tandem sequence as well.

Alternatively, host cells which contain the coding sequence for HITP and express HITP may be identified by a variety of procedures known to those of skill in the art. These procedures include, but are not limited to, DNA—DNA or DNA-RNA hybridization and protein bioassay or immunoassay techniques which include membrane, solution, or chip based technologies for the detection and/or quantification of the nucleic acid or protein.

The presence of the polynucleotide sequence encoding HITP can be detected by DNA—DNA or DNA-RNA hybridization or amplification using probes, portions or fragments of the sequence encoding HITP. Nucleic acid amplification based assays involve the use of oligonucleotides or oligomers based on the nucleic acid sequence to detect transformants containing DNA or RNA encoding HITP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of HITP, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HITP is preferred, but a competitive binding assay may be employed. These and other assays are described, among other places, in Hampton R et al (1990, *Serological Methods, a Laboratory Manual*, APS Press, St Paul Minn.) and Maddox DE et al (1983, J Exp Med 158:1211).

A wide variety of labels and conjugation techniques are known by those skilled in the art and can be used in various nucleic acid and amino acid assays. Means for producing labeled hybridization or PCR probes for detecting related sequences include oligolabeling, nick translation, end-labeling or PCR amplification using a labeled nucleotide. Alternatively, the HITP-encoding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 incorporated herein by reference.

Purification of HITP

Host cells transformed with a nucleotide sequence encoding HITP may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing HITP-encoding sequence can be designed with signal sequences which direct secretion of HITP through a prokaryotic or eukaryotic cell membrane. Other recombinant constructions may join the sequence encoding HITP to nucleotide sequence encoding a polypeptide domain which will facilitate purification of soluble proteins (Kroll DJ et al (1993) DNA Cell Biol 12:441–53; cf discussion of vectors infra containing fusion proteins).

HITP may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and HITP is useful to facilitate purification. One such expression vector provides for expression of a fusion protein comprising the sequence encoding HITP and nucleic acid sequence encoding 6 histidine residues followed by thioredoxin and an enterokinase cleavage site. The histidine residues facilitate purification while the enterokinase cleavage site provides a means for purifying HITP from the fusion protein.

In addition to recombinant production, fragments of HITP may be produced by direct peptide synthesis using solid-phase techniques (CF Stewart et al (1969) *Solid-Phase Peptide Synthesis*, WH Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of HITP may be chemically synthesized separately and combined using chemical methods to produce the full length molecule.

Uses of HITP

The rationale for use of the nucleotide and peptide sequences disclosed herein is based on the chemical and structural homology among the novel human induced tumor protein and Diff 33(GI 1293563; Dakuor and Morrish, supra), mouse testicular tumor protein (GI 459890; Lebel and Mes-Masson, supra), and the rat developmentally regulated protein (GI 310100; Pfeiffer, supra).

The overexpression of HITP in melanoma or other cancers, particularly carcinomas of the breast, colon and brain, makes the nucleic and amino acid sequences useful in the development of tumor diagnostics. The nucleotide sequence may be used in hybridization or PCR technologies to diagnose the induced expression of protective native sequences early in the disease process. Likewise, the protein can be used to produce antibodies useful in ELISA assays or a derivative diagnostic format.

The nucleotide sequence encoding HITP is useful when placed in an expression vector for making quantities of protein for therapeutic use. It is also potentially useful in vectors designed for gene therapy directed at melanomas and other cancers. Even the transient expression or delivery of HITP to cells and tissues locked in a cancer-producing cell cycle may direct the terminal differentiation of those cells, thereby stopping the progression, growth and development, of the cancers.

HITP Antibodies

HITP-specific antibodies are useful for the diagnosis and treatment of conditions and diseases associated with expression of HITP. Such antibodies include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

HITP for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of HITP amino acids may be fused with those of another protein such as keyhole limpet hemocyanin and antibody produced against the chimeric molecule. Procedures well known in the art can be used for the production of antibodies to HITP For the production of antibodies, various hosts including goats, rabbits, rats, mice, etc may be immunized by injection with HITP or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to HITP may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc. New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce HITP-specific single chain antibodies Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for HITP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse WD et al (1989) Science 256:1275–1281).

A variety of protocols for competitive binding or immunoradiometric assays using either polyclonal or monoclonal antibodies with established specificities are well known in the art. Such immunoassays typically involve the formation of complexes between HITP and its specific antibody and the measurement of complex formation. A two-site, monoclonal-based immunoassay utilizing monoclonal antibodies reactive to two noninterfering epitopes on a specific HITP protein is preferred, but a competitive binding assay may also be employed. These assays are described in Maddox DE et al (1983, J Exp Med 158:1211).

Diagnostic Assays Using HITP Specific Antibodies

Particular HITP antibodies are useful for the diagnosis of conditions or diseases characterized by expression of HITP or in assays to monitor patients being treated with HITP, its fragments, agonists or inhibitors. Diagnostic assays for HITP include methods utilizing the antibody and a label to detect HITP in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring HITP, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on HITP is preferred, but a competitive binding assay may be employed. These assays are described, among other places, in Maddox, DE et al (1983, J Exp Med 158:1211).

In order to provide a basis for diagnosis, normal or standard values for HITP expression must be established. This is accomplished by combining body fluids or cell extracts taken from normal subjects, either animal or human, with antibody to HITP under conditions suitable for complex formation which are well known in the art. The amount of standard complex formation may be quantified by comparing various artificial membranes containing known quantities of HITP with both control and disease samples from biopsied tissues. Then, standard values obtained from normal samples may be compared with values obtained from samples from subjects potentially affected by disease. Deviation between standard and subject values establishes the presence of disease state.

Drug Screening

HITP, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between HITP and the agent being tested, may be measured.

Another technique for drug screening which may be used for high throughput screening of compounds having suitable binding affinity to the HITP is described in detail in "Determination of Amino Acid Sequence Antigenicity" by Geysen HN, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of HITP and washed. Bound HITP is then detected by methods well known in the art. Substantially purified HITP can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding HITP specifically compete with a test compound for binding HITP. In this manner, the antibodies can be used to detect the presence of any peptide which shares one or more antigenic determinants with HITP.

Uses of the Polynucleotide Encoding HITP

A polynucleotide sequence encoding HITP or any part thereof may be used for diagnostic and/or therapeutic purposes. For diagnostic purposes, the sequence encoding HITP of this invention may be used to detect and quantitate gene expression in biopsied tissues in which HITP may be expressed in response to oncogenes. The diagnostic assay is useful to distinguish between absence, presence, and excess expression of HITP and to monitor regulation of HITP levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding HITP or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring HITP, alleles or related sequences.

Probes may also be used for the detection of related sequences and should preferably contain at least 50% of the nucleotides from any of these HITP-encoding sequences. The hybridization probes of the subject invention may be derived from the nucleotide sequence of SEQ ID NO:2 or from genomic sequence including promoter, enhancer elements and introns of the naturally occurring sequence encoding HITP. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for DNAs include the cloning of nucleic acid sequences encoding HITP or HITP derivatives into vectors for the production of mRNA probes. Such vectors are known in the art and are commercially available and may be used to synthesize RNA probes in vitro by means of the addition of the appropriate RNA polymerase such as T7 or SP6 RNA polymerase and the appropriate radioactively labeled nucleotides.

Diagnostic Use

Polynucleotide sequences encoding HITP may be used for the diagnosis of conditions or diseases with which the expression of HITP is associated. For example, polynucleotide sequences encoding HITP may be used in hybridization or PCR assays of fluids or tissues from biopsies to detect HITP expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The HITP-encoding nucleotide sequences disclosed herein provide the basis for assays that detect activation or induction associated with inflammation or disease. The nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of nucleotide sequences encoding HITP in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for HITP expression must be established. This is accomplished by combining body fluids or cell extracts taken from normal subjects, either animal or human, with HITP, or a portion thereof, under conditions suitable for hybridization or amplification. Standard hybridization may be quantified by comparing the values obtained for normal subjects with a dilution series of HITP run in the same experiment where a known amount of substantially purified HITP is used. Standard values obtained from normal samples may be compared with values obtained from samples from patients affected by HITP-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR may be used as described in U.S. Pat. Nos. 4,683,195 and 4,965,188 provides additional uses for oligonucleotides based upon the sequence encoding HITP. Such oligomers are generally chemically synthesized, but they may be generated enzymatically or produced from a recombinant source. Oligomers generally comprise two nucleotide sequences, one with sense orientation (5'→3') and one with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby PC et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to Diff 33 and its expression profile, the polynucleotide encoding HITP disclosed herein may be useful in the treatment of melanomas and other cancers, particularly carcinomas of the brain, breast or colon.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense of the sequence encoding HITP. See, for example, the techniques described in Sambrook et al (supra) and Ausubel et al (supra).

The polynucleotides comprising full length cDNA sequence and/or its regulatory elements enable researchers to use the sequence encoding HITP as an investigative tool in sense (Youssoufian H and HF Lodish 1993 Mol Cell Biol 13:98–104l) or antisense (Eguchi et al (1991l) Annu Rev Biochem 60:631–652) regulation of gene function. Such technology is now well known in the art, and sense or antisense oligomers, or larger fragments, can be designed from various locations along the coding or control regions.

Genes encoding HITP can be turned off by transfecting a cell or tissue with expression vectors which express high levels of a desired HITP fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of the sequence encoding HITP, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee JE et al (In: Huber BE and BI Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of the sequence encoding HITP.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HITP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences encoding HITP disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence encoding HITP can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price CM (1993; Blood Rev 7:127–34) and Trask BJ (1991; Trends Genet 7:149–54).

The technique of fluorescent in situ hybridization of chromosome spreads has been described, among other places, in Verma et al (1988) *Human Chromosomes: A Manual of Basic Techniques*, Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a the sequence encoding HITP on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson TJ et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22-23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of HTTP, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration to animals, but more preferably, humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that HTTP can be used as a therapeutic molecule to force differentiation and stop the cell cycle which contributes to the growth of cancerous cells or tissues.

The examples below are provided to illustrate the subject invention and are not included for the purpose of limiting the invention.

EXAMPLES

I cDNA Library Construction

The BRAINOT03 cDNA library was constructed from normal brain tissue removed from a 26 year old male (lot #0003; Mayo Clinic, Rochester Minn.). The frozen tissue was homogenized and lysed using a Brinkmann Homogenizer Polytron PT-3000 (Brinkmann Instruments, Westbury N.J.). The reagents and extraction procedures were used as supplied in the Stratagene RNA Isolation Kit (Cat. # 200345; Stratagene). The lysate was centrifuged over a 5.7M CsCl cushion using an Beckman SW28 rotor in a Beckman L8-70M Ultracentrifuge (Beckman Instruments) for 18 hours at 25,000 rpm at ambient temperature. The RNA was extracted once with phenol chloroform pH 8.0, once with acid phenol pH 4.0, precipitated using 0.3M sodium acetate and 2.5 volumes of ethanol, resuspended in water and DNase treated for 15 min at 37° C. The RNA was isolated using the Qiagen Oligotex kit (QIAGEN Inc. Chatsworth Calif.) and used to construct the cDNA library.

The RNA was handled according to the recommended protocols in the SuperScript Plasmid System for cDNA Synthesis and Plasmid Cloning (Cat. #18248-013; Gibco/BRL). cDNAs were fractionated on a Sepharose CL4B column (Cat. #275105, Pharmacia), and those cDNAs exceeding 400 bp were ligated into pSport I. The plasmid pSport I was subsequently transformed into DH5a™ competent cells (Cat. #18258-012, Gibco/BRL).

II Isolation and Sequencing of cDNA Clones

Plasmid DNA was released from the cells and purified using the Miniprep Kit (Cat. #77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Cat. #22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J Mol Biol 94:441f), using a Hamilton Micro Lab 2200 (Hamilton, Reno Nev.) in combination with four Peltier Thermal Cyclers (PTC200; MJ Research, Watertown Mass.) and Applied Biosystems 377 DNA Sequencing Systems (Perkin Elmer), and reading frame was determined.

III Homology Searching of cDNA Clones and Their Deduced Proteins

Each cDNA was compared to sequences in GenBank using a search algorithm developed by Applied Biosystems and incorporated into the INHERIT-670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul SF (1993) J Mol Evol 36:290–300; Altschul, SF et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al. supra).

Analogous computer techniques using BLAST (Altschul SF 1993 and 1990, supra) are used to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of the Sequence Encoding HTTP

The nucleic acid sequence of SEQ ID NO:2 is used to design oligonucleotide primers for extending a partial nucleotide sequence to full length or for obtaining 5'sequence from genomic libraries. One primer is synthesized to initiate extension in the antisense direction (XLR) and the other is synthesized to extend sequence in the sense direction (XLF). Primers allow the extension of the known sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| Step 1 | 940° C. for 1 min (initial denaturation) |
| --- | --- |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQuick™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook J et al. supra). After incubation for one hour at 37° C., the whole transformation mixture is plated on Luria Bertani (LB)-agar (Sambrook J et al. supra) containing 2×Carb. The following day, several colonies are randomly picked from each plate and cultured in 150 µl of liquid LB/2×Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |

-continued

| Step 5 | Repeat steps 2–4 for an additional 29 cycles |
| --- | --- |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of $[\gamma\text{-}^{32}P]$ adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The sequence encoding HITP, or any part thereof, is used to inhibit in vivo or in vitro expression of naturally occurring sequence. Although use of antisense oligonucleotides, comprising about 20 base-pairs, is specifically described, essentially the same procedure is used with larger cDNA fragments. An oligonucleotide complementary to the coding sequence of HITP as shown in FIGS. 1A, 1B, 1C, and 1D is used to inhibit expression of naturally occurring sequence. The complementary oligonucleotide is designed from the most unique 5' sequence as shown in FIGS. 1A, 1B, 1C, and 1D and used either to inhibit transcription by preventing promoter binding to the upstream nontranslated sequence or translation of an HITP-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A, 1B, 1C, and 1D.

VIII Expression of HITP

Expression of the HITP is accomplished by subcloning the cDNAs into appropriate vectors and transfecting the vectors into host cells. In this case, the cloning vector, pSport, previously used for the generation of the cDNA library is used to express HITP in *E. coli*. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length HITP. The signal sequence directs the secretion of HITP into the bacterial growth media which can be used directly in the following assay for activity.

IX Assay for HITP Activity

HITP activity can be assayed in vitro using any appropriate commercially available immortalized or neoplastic cell line. Vectors expressing the nucleic acid sequence or purified HITP can be delivered to the cells using technologies well known in the art. The activity of HITP is assayed two days after treatment by using stains well known in the art to stain untreated and treated cell samples and observing differences in cell division index. A lower cell cycle index indicates that HITP has stopped the cell cycle.

An extension of this assay can be used to compare the cell cycle indices of biopsied cells from a patient before and after treatment with a pharmaceutical composition containing purified HITP and a suitable pharmaceutical excipient. Methods of delivering or using the pharmaceutical composition may also be evaluated employing this assay.

X Production of HITP Specific Antibodies

HITP substantially purified using PAGE electrophoresis (Sambrook, supra) is used to immunize rabbits and to produce antibodies using standard protocols. The amino acid sequence translated from HITP is analyzed using DNAStar software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (shown in FIGS. 4, 5A, and 5B) is described by Ausubel FM et al (supra).

Typically, the oligopeptides are 15 residues in length, synthesized 40 using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel FM et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HITP Using Specific Antibodies

Naturally occurring or recombinant HITP is substantially purified by immunoaffinity chromatography using antibodies specific for HITP. An immunoaffinity column is constructed by covalently coupling HITP antibody to an activated chromatographic resin such as CnBr-activated Sepharose (Pharmacia Biotech). After the coupling, the resin is blocked and washed according to the manufacturer's instructions.

Membrane fractions from cells expressing HITP are prepared by methods well known in the art. Alternatively, a recombinant HITP fragment containing an appropriate signal sequence may be secreted in useful quantitiy into the medium in which transfected cells are grown.

A HITP-containing preparation is passed over the immunoaffinity column, and the column is washed under conditions that allow the preferential absorbance of HITP (eg, high ionic strength buffers in the presence of detergent). The column is eluted under conditions that disrupt antibody/HITP binding (eg, a buffer of pH 2–3 or a high concentration of a chaotrope such as urea or thiocyanate ion), and HITP is collected.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. An isolated and purified polynucleotide sequence encoding the polypeptide comprising the amino acid sequence of SEQ ID NO:1.

2. An isolated polynucleotide sequence consisting of the nucleic acid sequence of SEQ ID NO:2.

3. An isolated polynucleotide sequence consisting of the complement of SEQ ID NO:2.

4. A hybridization probe consisting of SEQ ID NO:2.

5. A recombinant expression vector containing the polynucleotide sequence of claim 2.

6. A recombinant host cell containing the polynucleotide sequence of claim 2.

7. A method for producing the polypeptide consisting of SEQ ID NO: 1, the method comprising the steps of:

a) culturing the host cell of claim 6 under conditions suitable for the expression of the polypeptide; and b) recovering the polypeptide from the host cell culture.

* * * * *